US012592063B2

(12) United States Patent
Li et al.

(10) Patent No.: US 12,592,063 B2
(45) Date of Patent: Mar. 31, 2026

(54) MACHINE LEARNING OF SPATIO-TEMPORAL MANIFOLDS FOR SOURCE-FREE VIDEO DOMAIN ADAPTATION

(71) Applicant: NEC Laboratories America, Inc., Princeton, NJ (US)

(72) Inventors: Kai Li, Plainsboro, NJ (US); Deep Patel, Franklin Park, NJ (US); Erik Kruus, Hillsborough, NJ (US); Renqiang Min, Princeton, NJ (US)

(73) Assignee: NEC Corporation, Tokyo (JP)

( * ) Notice: Subject to any disclaimer, the term of this patent is extended or adjusted under 35 U.S.C. 154(b) by 287 days.

(21) Appl. No.: 18/504,469

(22) Filed: Nov. 8, 2023

(65) Prior Publication Data

US 2024/0161473 A1    May 16, 2024

Related U.S. Application Data

(60) Provisional application No. 63/425,327, filed on Nov. 15, 2022, provisional application No. 63/424,155, filed on Nov. 10, 2022.

(51) Int. Cl.
| | |
|---|---|
| *G06V 10/774* | (2022.01) |
| *G06V 10/75* | (2022.01) |
| *G06V 20/40* | (2022.01) |
| *G16H 15/00* | (2018.01) |

(52) U.S. Cl.
CPC ........ *G06V 10/7753* (2022.01); *G06V 10/751* (2022.01); *G06V 20/44* (2022.01); *G16H 15/00* (2018.01)

(58) Field of Classification Search
CPC ...................................................... G06V 20/44
See application file for complete search history.

(56) References Cited

PUBLICATIONS

Temporal Consistency Learning of Inter-Frames for Video Super-Resolution, arXiv:2211.01639v1 [cs.CV] Nov. 3, 2022 (Year: 2022).*
Guo, Jun, and Hongyang Chao. "Building an end-to-end spatial-temporal convolutional network for video super-resolution." Proceedings of the AAAI conference on artificial intelligence. vol. 31. No. 1. 2017. (Year: 2017).*

(Continued)

*Primary Examiner* — Raphael Schwartz
(74) *Attorney, Agent, or Firm* — Vincent Duffy; Joseph Kolodka

(57) ABSTRACT

Methods and systems for training a model include performing spatial augmentation on an unlabeled input video to generate spatially augmented video. Temporal augmentation is performed on the input video to generate temporally augmented video. Predictions are generated, using a model that was pre-trained on a labeled dataset, for the unlabeled input video, the spatially augmented video, and the temporally augmented video. Parameters of the model are adapted using the predictions while enforcing temporal consistency, temporal consistency, and historical consistency. The model may be used for action recognition in a healthcare context, with recognition results being used for determining whether patients are performing a rehabilitation exercise correctly.

16 Claims, 8 Drawing Sheets

(56) References Cited

PUBLICATIONS

Liang et al., "Do We Really Need to Access the Source Data? Source Hypothesis Transfer for Unsupervised Domain Adaptation", arXiv:2002.08546v6 [cs.CV] Jun. 1, 2021, pp. 1-12.
Xu et al., "Source-free Video Domain Adaptation by Learning Temporal Consistency for Action Recognition", arXiv:2203. 04559v4 [cs.CV] Jul. 11, 2022, pp. 1-17.

* cited by examiner

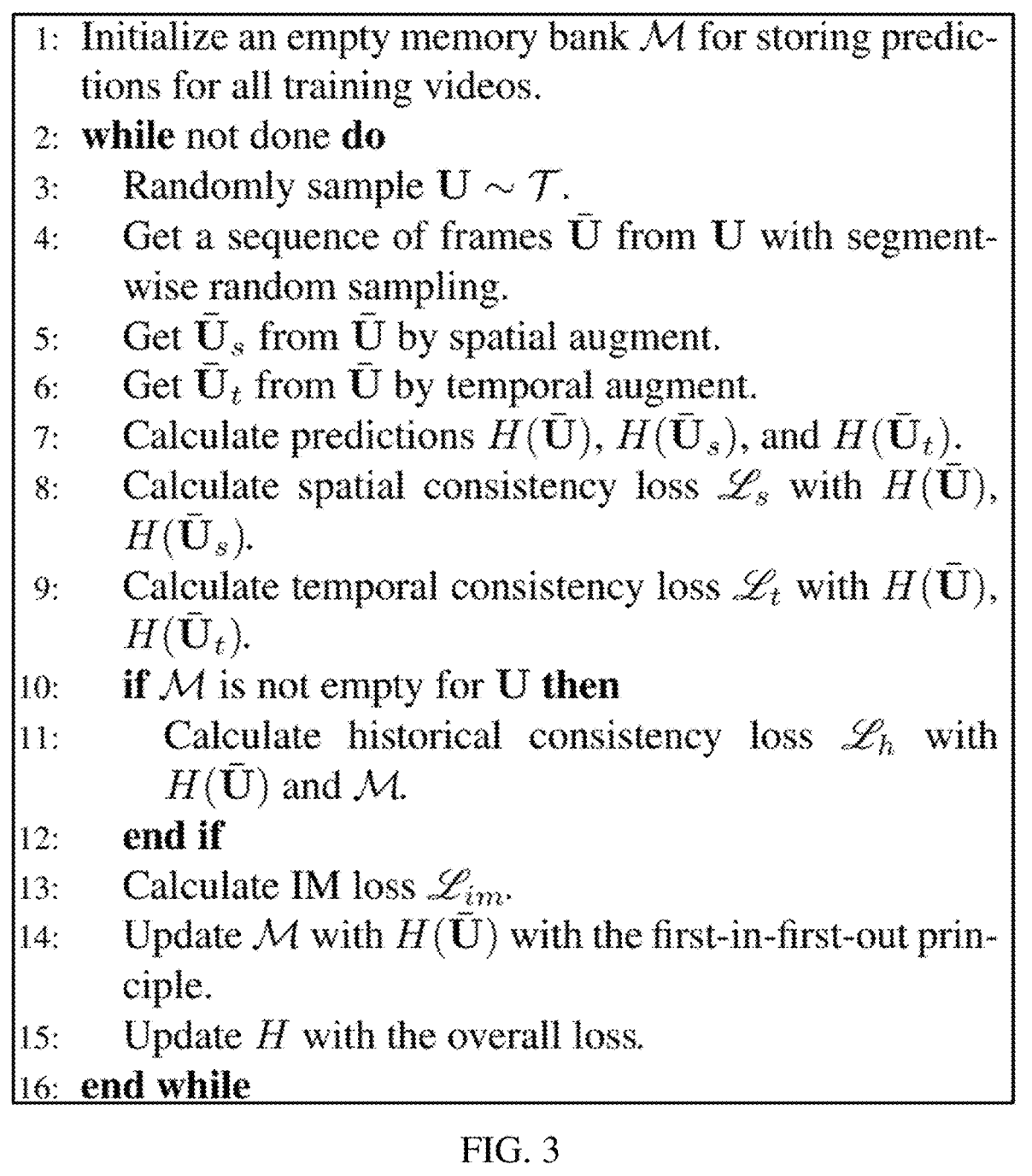

1: Initialize an empty memory bank $\mathcal{M}$ for storing predictions for all training videos.

2: while not done do

3:    Randomly sample $\mathbf{U} \sim \mathcal{T}$.

4:    Get a sequence of frames $\bar{\mathbf{U}}$ from $\mathbf{U}$ with segment-wise random sampling.

5:    Get $\bar{\mathbf{U}}_s$ from $\bar{\mathbf{U}}$ by spatial augment.

6:    Get $\bar{\mathbf{U}}_t$ from $\bar{\mathbf{U}}$ by temporal augment.

7:    Calculate predictions $H(\bar{\mathbf{U}})$, $H(\bar{\mathbf{U}}_s)$, and $H(\bar{\mathbf{U}}_t)$.

8:    Calculate spatial consistency loss $\mathcal{L}_s$ with $H(\bar{\mathbf{U}})$, $H(\bar{\mathbf{U}}_s)$.

9:    Calculate temporal consistency loss $\mathcal{L}_t$ with $H(\bar{\mathbf{U}})$, $H(\bar{\mathbf{U}}_t)$.

10:    if $\mathcal{M}$ is not empty for $\mathbf{U}$ then

11:       Calculate historical consistency loss $\mathcal{L}_h$ with $H(\bar{\mathbf{U}})$ and $\mathcal{M}$.

12:    end if

13:    Calculate IM loss $\mathcal{L}_{im}$.

14:    Update $\mathcal{M}$ with $H(\bar{\mathbf{U}})$ with the first-in-first-out principle.

15:    Update $H$ with the overall loss.

16: end while

FIG. 3

Pre-train model with labeled videos
402

Adapt model with unlabeled videos
404

Training model
400

Deploy model
410

Record video
420

Classify action(s)
430

Generate report
440

MACHINE LEARNING OF SPATIO-TEMPORAL MANIFOLDS FOR SOURCE-FREE VIDEO DOMAIN ADAPTATION

RELATED APPLICATION INFORMATION

This application claims priority to U.S. Patent Application No. 63/424,155, filed on Nov. 10, 2022, and to U.S. Patent Application No. 63/425,327, filed on Nov. 15, 2022, each incorporated herein by reference in its entirety.

BACKGROUND

Technical Field

The present invention relates to action recognition and, more particularly, to learning manifolds for video domain adaptation.

Description of the Related Art

Action recognition is a task used in automated video understanding that identifies an action that is being performed in a video sequence. However, an action recognition model that is trained with annotated data drawn from one statistical distribution may show decreased performance when tested on data outside that distribution.

SUMMARY

A method for training a model includes training a model include performing spatial augmentation on an unlabeled input video to generate spatially augmented video. Temporal augmentation is performed on the input video to generate temporally augmented video. Predictions are generated, using a model that was pre-trained on a labeled dataset, for the unlabeled input video, the spatially augmented video, and the temporally augmented video. Parameters of the model are adapted using the predictions while enforcing temporal consistency, temporal consistency, and historical consistency.

A system for training a model includes a hardware processor and a memory that stores a computer program. When executed by the hardware processor, the computer program causes the hardware processor to perform spatial augmentation on an unlabeled input video to generate spatially augmented video, to perform temporal augmentation on the input video to generate temporally augmented video, to generate predictions, using a model that was pre-trained on a labeled dataset, for the unlabeled input video, the spatially augmented video, and the temporally augmented video, and to adapt parameters of the model using the predictions while enforcing temporal consistency, temporal consistency, and historical consistency.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 3 is pseudo-code for updating the parameters of a pre-trained action recognition model based on spatial, temporal, and historical consistency, in accordance with an embodiment of the present invention;

DETAILED DESCRIPTION OF PREFERRED EMBODIMENTS

Unsupervised video domain adaptation (UVDA) learns an adaptive model using labeled video data from a source domain and unlabeled video data from a target domain. UVDA may take input videos from both domains and train a model by minimizing a classification risk on labeled source videos, aligning videos from both domains in a class-agnostic fashion. As described herein, spatio-temporal manifolds (STEMs) may be learned, where actions of a same category may be drawn from the same low-dimensional manifold, regardless of spatio-temporal variance in the high-dimensional space. As used herein, the term "manifold" refers to a space of a given dimensionality, such that high-dimensional video data may be projected into a low-dimensional space, where videos in a same class are located close to one another in the low-dimensional space. A spatial-temporal-historical consistency (STHC) model trained in a source domain may thereby be adapted encouraging it to handle spatio-temporal variance by learning such low-dimensional manifolds.

It can be challenging to learn reliable manifold structures without label supervision. To mitigate this, spatial and temporal data augmentation may be performed. For each unlabeled target video, spatial and temporal augmentations may be applied in a stochastic manner to produce augmented videos that outline the neighboring structure of the manifold that the video resides on. Encouraging consistent classification predictions for the video and its augmented versions ensures that they are drawn from the same spatio-temporal manifold. With these learned manifolds, the model can generalize to the unlabeled target domain and can make consistent predictions for videos drawn from the same manifold.

The models described herein may be used to implement, for example, action recognition within a video stream. Such action recognition may be used for a variety of applications, such as sports analysis and training, industrial training, and health and rehabilitation. For example, video may be taken of a patient undergoing physical therapy and action recognition may be used to identify the patient's form and whether they are performing an exercise correctly. This information may then be used to inform medical decision making, for example with a healthcare professional making changes to the patient's physical therapy and rehabilitation regimen.

Figure 1:
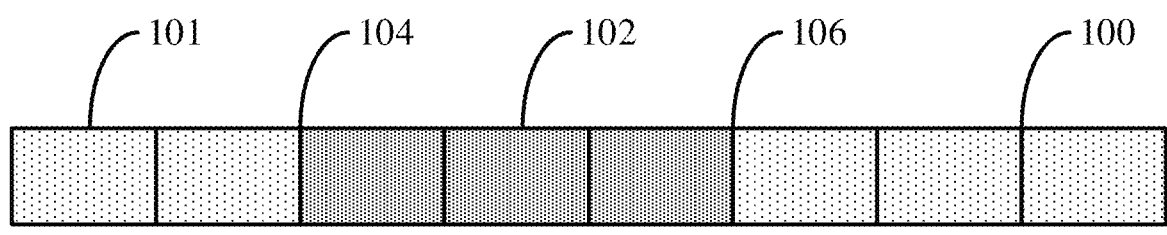
FIG. 1 is a diagram of a video that includes a series of frames portraying an action, in accordance with an embodiment of the present invention.

Referring now to FIG. 1, an exemplary video stream 100 is illustrated, being made up of a series of sequential video frames 101. Each video frame 101 may include an image that captures a camera's view at a particular time. Included in the video stream 100 is a series of action frames 102 that show a particular action taking place. The action frames 102 have a beginning time 104 and an ending time 106.

The video stream 100 may include labels that explicitly indicate the beginning time 104 and the ending time 106 of an action, and may further include a label that identifies the action taking place in the action frames 102. In an unannotated video stream, the video stream 100 may lack labels for these time markers and classes.

Each frame 101 includes multiple kinds of information. For example, each frame 101 may include appearance information that includes RGB values for each pixel of the frame 101, or any other appropriate encoding of static visual information. In addition, more than one frame 101 may be considered together to identify motion information, for example by identifying optical flow information that captures dynamic and motion information from one frame 101 to the next.

In one example of a video stream 100, the video stream 100 may capture a sporting event, such as a long jump. The action frames 102 may show the actual jump taking place, while frames 101 before and after the action frames 102 may show related or unrelated activity, such as the jumper's run leading up to the jump and the jumper landing and walking away.

Source-free video domain adaptation (SFVDA) may be derived from UVDA, sharing the same goal of learning an adaptive video classification model H using a source dataset $S=\{(X_1, y_1), (X_2, y_2), \ldots, (X_M, y_M)\}$ of M labeled videos X having respective labels y and a target dataset $T=\{U_1, U_2, \ldots, U_N\}$ of N unlabeled videos. In SFVDA, H is learned in two steps, with a pertaining step learning weights using the source domain data S in a supervised fashion and with an adaptation step that adapts the pretrained weights to the target domain using T in an unsupervised fashion. Separating S from the adaptation process prevents the labeled data from being disclosed, enabling privacy-safe adaptation.

The model H may be decoupled as $H=F\circ G\circ C$, where F, G, and C are a frame feature extractor, a temporal feature extractor, and a classifier, respectively. For each video (X, y)$\in$S, segment-wise frame sampling may be performed, with $X=\{x_1, x_2, \ldots, x_M\}$ being the m frames of the video. The frames may be evenly divided into K segments, and one sample from each segment may be taken. This produces a K-frame video snippet of class y $(\overline{X}, y)$, where $|\overline{X}|=K$. Using $\overline{X}$ as input to F produces a sequence of frame features, which are then processed by G to learn temporal information. Average pooling of all frame features may be performed to get a vector representation for $\overline{X}$, which may be used as input to the classifier C to calculate a cross-entropy loss with y and to update H with stochastic gradient descent and back-propagation.

Given a model H with pretrained weights learned from the labeled source data S, the STHC model adapts the weights to the target domain using unlabeled data T. This is accomplished by learning spatial-temporal manifolds that videos from a same category are mapped to, despite spatio-temporal variance. The model H can thereby surpass the domain gap between the source domain and the target domain to achieve better generalization performance. To learn such manifolds, a number of spatially or temporally augmented videos are generated for each target video using stochastic augmentation. Consistent predictions are enforced for the video and its augmented versions from spatial, temporal, and historical points of view.

Figure 2:
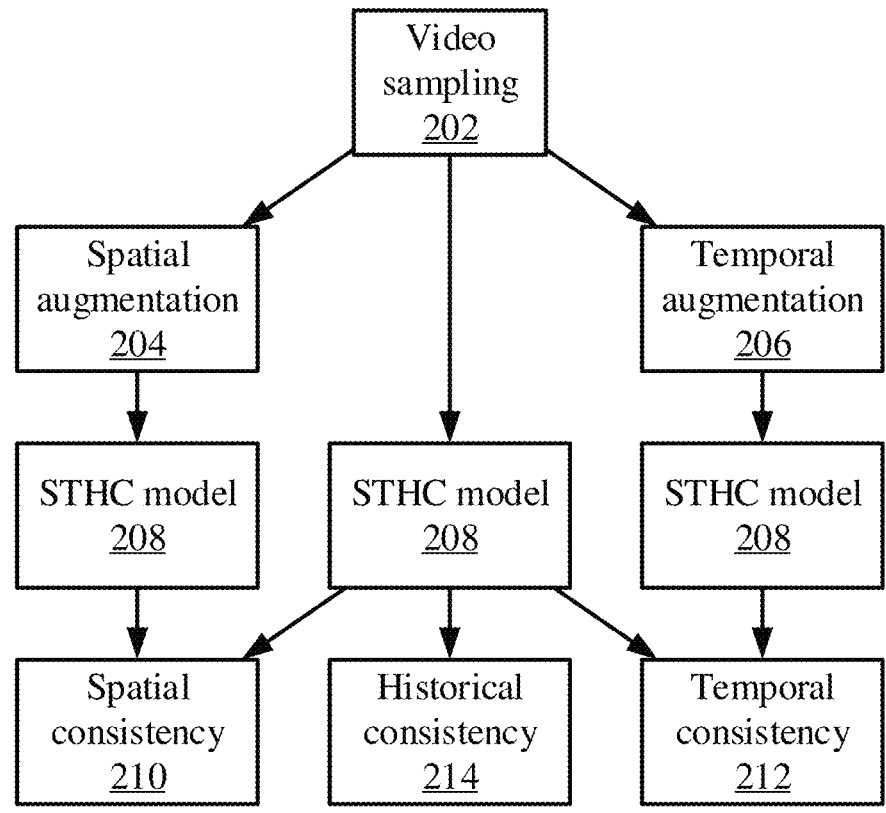
FIG. 2 is a diagram of a training framework for an action recognition model that includes spatial, temporal, and historical consistency constraints, in accordance with an embodiment of the present invention.

Referring now to FIG. 2, a block diagram of a STHC model framework is shown. An unlabeled video U$\in$T, having N frames, is sampled into k parts by block 202, with one frame being randomly selected from each part to produce a K-frame sequence $\overline{U}=\{u_1, u_2, \ldots u_K\}$. The sequence is processed by spatial augmentation 204 to generate spatially augmented video and by temporal augmentation 206 to generate temporally augmented video. The unlabeled video 202, the output of spatial augmentation 204, and the output of temporal augmentation 206 are each independently processed by a pre-trained STHC model 208.

Per-frame spatial augmentation 204 may be performed to generate $\overline{U}_s=\{\psi(u_1), \psi(u_2), \ldots, \psi(u_N)\}$, where $\psi$ is a stochastic spatial augmentation function, implying that different augmented frames can be obtained if $\psi$ is applied to a same frame at different times. The stochastic function can thereby generate potentially infinite augmented videos around $\overline{U}$ in the low-dimensional manifold space, which enables more precise modeling of the manifold.

In some embodiments, the spatial augmentation 204 may include a random combination of image transformations, which may be selected from a pool that includes color inversion, translation, and adjustment. In some embodiments, the spatial augmentation 204 may include a removal of image information, for example by replacing a random square patch of a frame with gray pixels.

The spatially augmented video sequence $\overline{U}_s$ may be spatially adjacent with $\overline{U}$ in the low-dimensional manifold space, as it is generated from $\overline{U}_s$ with frame content perturbed. The semantic category information, such as the actions that are shown in the video, should be preserved.

A spatial proximity constraint may be enforced to ensure spatial consistency in block 210, for example by minimizing the discrepancy between the classification predictions of $\overline{U}_s$ and $\overline{U}$ as:

$$\mathcal{L}_s=s(H(\overline{U}),H(\overline{U}_s))$$

where s($\bullet,\bullet$) is a prediction consistency measurement function. Exemplary consistency measurement functions include cross-entropy, Kullback-Leibler divergence, and cosine similarity. The Kullback-Leibler divergence may be used in particular, but should not be considered limiting.

A temporal proximity constraint may similarly be enforced to ensure temporal consistency in block 212. For the sampled frame sequence $\overline{U}$, stochastic temporal augmentation 206 may be applied to generate $\overline{U}_t=\{\phi(u_1), \phi(u_2), \ldots, \phi(u_K)\}$, where $\phi$ denotes a stochastic temporal function that drops $u_k$ out of the sequence, for example at a rate of 0.5. This makes $\overline{U}_t$ a sparser version of $\overline{U}$. Despite having fewer frames, it is expected that $\overline{U}_t$ will preserve the motion dynamics of $\overline{U}$ in the low-dimensional manifold space, which helps learn the neighboring manifold structure of $\overline{U}$. As $\overline{U}_t$ may be viewed as a harder version of $\overline{U}$, with different motion dynamics, enforcing prediction consistency between them encourages the model to surpass the motion dynamics variations between domains and to facilitate model adaptation.

As with spatial consistency 210, temporal proximity may be enforced in block 212 by minimizing the discrepancy between the classification predictions U and $U_t$ as:

$$\mathcal{L}_T = s(H(U), H(U_t))$$

where s(•,•) is the same affinity function as was used in the spatial consistency 210.

Historical consistency 214 is used to reinforce the temporal consistency 212. Given that U is randomly sampled from the k video segments, the temporally augmented $U_t$ is generated to encourage temporal consistency by masking some frames to make a hard augmented version. However, when the video is long or the segment number k is small, the variance within each segment may be large, which the temporal consistency described above does not take into account.

In each training round, the past sequences can be viewed as other versions of the current sequence, and consistency can be enforced between past predictions and the current prediction. A memory bank M may be used to store past Q predictions for each video. M may be used to calculate the historical consistency loss as:

$$\mathcal{L}_h = \mathbb{E}_{p_u \sim M}[s(p_u, H(U))]$$

where $p_u$ is a historical prediction for a video clip sampled from U. The value of Q should be kept small to prevent predictions from obsolete models from being stored, as enforcing consistency with old knowledge would prevent the model from learning new knowledge. An exemplary value of Q=2 reaches generalizable results.

During training, a learning objective may be formulated as $$\mathcal{L} = \mathcal{L}_{im} + \alpha(\mathbb{E}_{U \sim T}(\mathcal{L}_s + \mathcal{L}_t + \mathcal{L}_h))$$

where $\alpha$ is a hyper-parameter and $\mathcal{L}_{im}$ is an information maximization loss, such as:

$$\mathcal{L}_{im} = -\mathbb{E}_{U \sim T} \sum_{r=1}^{R} H(U) \log H(U) + \sum_{r=1}^{R} p_r \log(p_r)$$

where $p = -\mathbb{E}_{U \sim T} H(U)$ is the mean of predictions over all target videos, and where $p_r$ is the $r^{th}$ dimension of p. The first term of $\mathcal{L}_{im}$ minimizes the entropy of the probability, encouraging the model to make confident predictions, while the second term maximizes the entropy of p to encourage the samples to be balanced over all classes.

Referring now to FIG. 3, pseudo-code for adapting the parameters of an STHC model is shown, following the framework shown in FIG. 2.

Figure 4:
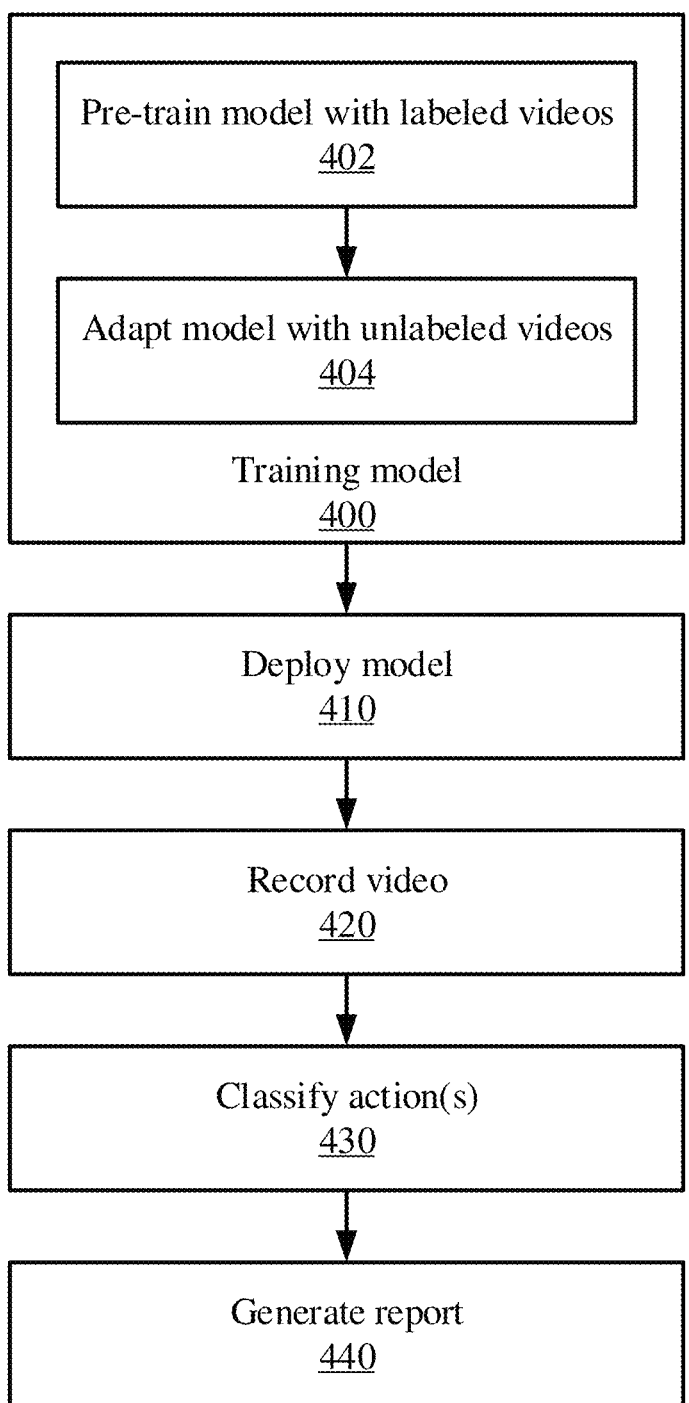
FIG. 4 is a block/flow diagram of a method for training and using an action recognition model, in accordance with an embodiment of the present invention.

Referring now to FIG. 4, a method for training the STHC model is shown. The model is trained in block 400 in a two-stage process. Block 402 begins by pre-training the model according to a labeled training dataset in a source domain. This training may be performed using supervised training of, for example, an action classifier that identifies an action performed in an input video.

Block 404 then adapts the model according to an unlabeled training dataset that may be in a target domain. For example, the target domain may include video taken under different lighting conditions or from a different viewpoint. By enforcing spatial, temporal, and historical consistency across different augmented versions of the videos in the unlabeled training dataset, the generalizability of the model can be increased while maintaining its efficacy in the source domain.

After the model is trained in block 400, the model may be deployed 410 for use, for example in a healthcare facility. New video may be recorded 420 and actions may be classified 430 in the new video relating to recorded motion of a person in the video. Block 440 generates a report relating to the recognized action(s).

The STHC model can be readily extended to other video domain adaptation problems. In partial domain adaptation, classes in the target domain may be a subset of classes in the source domain. Under a source-free constraint, this implies that only samples from a part of all the classes of the source domain are used to adapt the model. The STHC model can be directly applied to such a setting, as the consistency terms described above have no assumption on the class distributions of the target domain. The class-balancing term of $\mathcal{L}_{im}$ may be dropped in the partial domain adaptation setting.

In open-set domain adaptation, source classes may be a subset of the target classes. The entropy of predictions can be used as a measurement of uncertainty to divide target samples into groups, for example using K-means clustering. The group with higher mean uncertainty may be regarded as samples from unknown classes and may be rejected for adaptation.

In black box model adaptation, the source model may not be available for adaptation, but may instead serve as a black box that produces outputs for given inputs. The STHC model may be extended to this scenario with a two-stage solution. In a first stage, the black box model may be treated as a teacher model to train a student model of randomly initialized weights via knowledge distillation on target data. In the second stage, the student model may be adapted as above.

Figure 5:
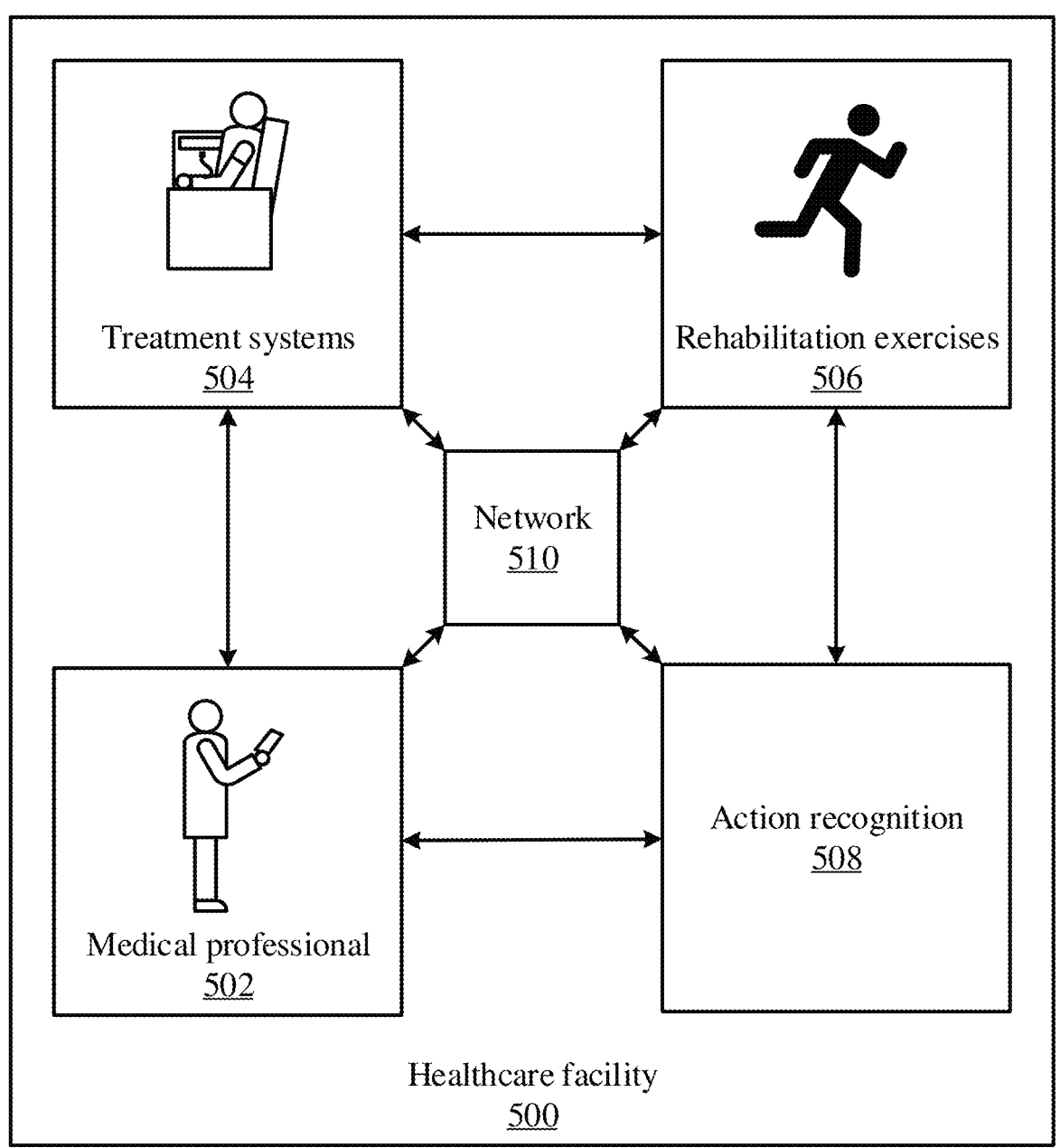
FIG. 5 is a block diagram of an exemplary application of an action recognition model in a healthcare facility, in accordance with an embodiment of the present invention.

Referring now to FIG. 5, a diagram of action recognition is shown in the context of a healthcare facility 500. A patient may perform rehabilitation exercises 506 at the healthcare facility 500, where their activity may be recorded with one or more video cameras. The rehabilitation exercises may make use of treatment systems 504, such as exercise equipment and biometric monitoring devices.

The healthcare facility may include one or more medical professionals 502 who provide information relating to the patient's rehabilitation progress and information provided by the treatment systems 504. As action recognition 508 is performed on the recorded rehabilitation exercises 506, information may be automatically generated regarding the patient's form. Ineffective or hazardous may be identified and a report may be generated for a medical professional 502 to use in decision making. For example, based on the report, the medical professional 502 may correct the patient's motion to aid in their further rehabilitation.

The different elements of the healthcare facility 500 may communicate with one another via a network 510, for example using any appropriate wired or wireless communications protocol and medium. The medical professional 502 may thereby receive information relating to the rehabilitation exercises 506 from the action recognition 508.

Figure 6:
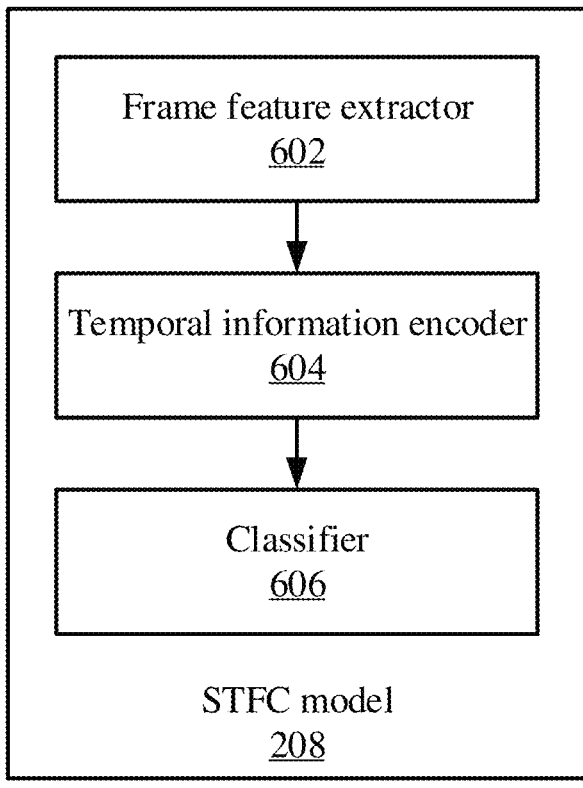
FIG. 6 is a block/flow diagram illustrating stages in an action recognition model, in accordance with an embodiment of the present invention.

Referring now to FIG. 6, additional detail on the STFC model 208 is shown. The model 208 includes a frame feature extractor 602 that generates features of each frame of an input video. The frame feature extractor 602 may include any appropriate image feature encoding model, such as a residual neural network (ResNet).

Temporal information encoder 604 captures information about the motion of elements within the video over time, and a classifier 606 uses this information to identify, for example, an action that is performed within the video. The temporal information encoder 604 takes input as a sequence of frame features, extracted by frame feature extractor 602, that represent the whole video. The temporal information encoder 604 may be implemented as a multi-layer perceptron (MLP) that models the interactions of temporal information among all the frames, with a mean pooling operator over all the frame features.

The classifier 606 takes the video feature as input and outputs a prediction score for the category that the video belongs to. The classifier 606 may be implemented as a single fully-connected layer.

Figure 7:
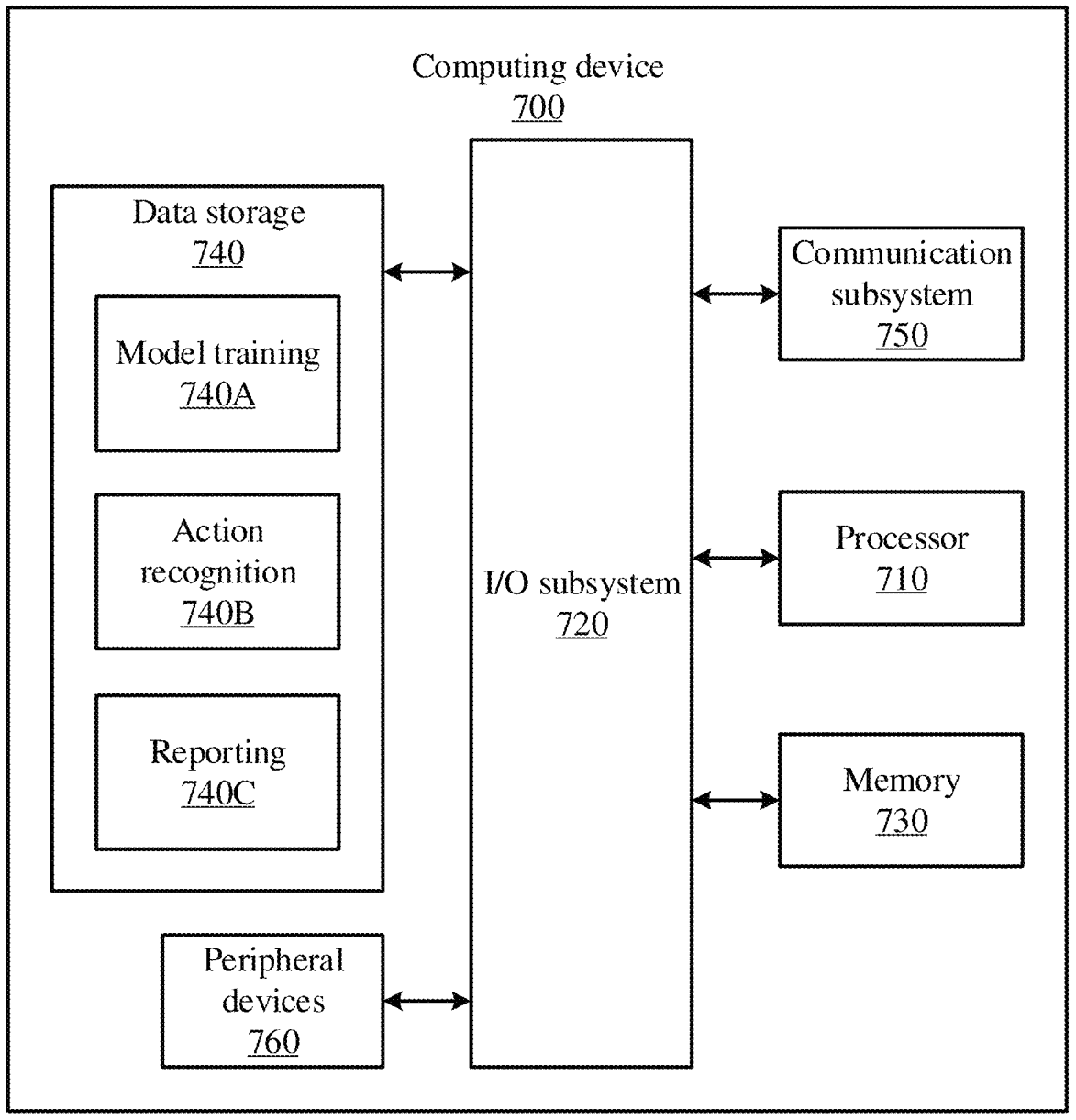
FIG. 7 is a block diagram of a computing device that can train and use an action recognition model, in accordance with an embodiment of the present invention.

Referring now to FIG. 7, an exemplary computing device 700 is shown, in accordance with an embodiment of the present invention. The computing device 700 is configured to perform action recognition.

The computing device 700 may be embodied as any type of computation or computer device capable of performing the functions described herein, including, without limitation, a computer, a server, a rack based server, a blade server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. Additionally or alternatively, the computing device 700 may be embodied as one or more compute sleds, memory sleds, or other racks, sleds, computing chassis, or other components of a physically disaggregated computing device.

As shown in FIG. 7, the computing device 700 illustratively includes the processor 710, an input/output subsystem 720, a memory 730, a data storage device 740, and a communication subsystem 750, and/or other components and devices commonly found in a server or similar computing device. The computing device 700 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 730, or portions thereof, may be incorporated in the processor 710 in some embodiments.

The processor 710 may be embodied as any type of processor capable of performing the functions described herein. The processor 710 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 730 may be embodied as any type of volatile or non-volatile memory or data storage capable of performing the functions described herein. In operation, the memory 730 may store various data and software used during operation of the computing device 700, such as operating systems, applications, programs, libraries, and drivers. The memory 730 is communicatively coupled to the processor 710 via the I/O subsystem 720, which may be embodied as circuitry and/or components to facilitate input/output operations with the processor 710, the memory 730, and other components of the computing device 700. For example, the I/O subsystem 720 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.), and/or other components and subsystems to facilitate the input/output operations. In some embodiments, the I/O subsystem 720 may form a portion of a system-on-a-chip (SOC) and be incorporated, along with the processor 710, the memory 730, and other components of the computing device 700, on a single integrated circuit chip.

The data storage device 740 may be embodied as any type of device or devices configured for short-term or long-term storage of data such as, for example, memory devices and circuits, memory cards, hard disk drives, solid state drives, or other data storage devices. The data storage device 740 can store program code 740A for training a model, 740B for recognizing actions within a video, and/or 740C for generating a report on the recognized actions. Any or all of these program code blocks may be included in a given computing system. The communication subsystem 750 of the computing device 700 may be embodied as any network interface controller or other communication circuit, device, or collection thereof, capable of enabling communications between the computing device 700 and other remote devices over a network. The communication subsystem 750 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 700 may also include one or more peripheral devices 760. The peripheral devices 760 may include any number of additional input/output devices, interface devices, and/or other peripheral devices. For example, in some embodiments, the peripheral devices 760 may include a display, touch screen, graphics circuitry, keyboard, mouse, speaker system, microphone, network interface, and/or other input/output devices, interface devices, and/or peripheral devices.

Of course, the computing device 700 may also include other elements (not shown), as readily contemplated by one of skill in the art, as well as omit certain elements. For example, various other sensors, input devices, and/or output devices can be included in computing device 700, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. These and other variations of the processing system 700 are readily contemplated by one of ordinary skill in the art given the teachings of the present invention provided herein.

Figure 8:
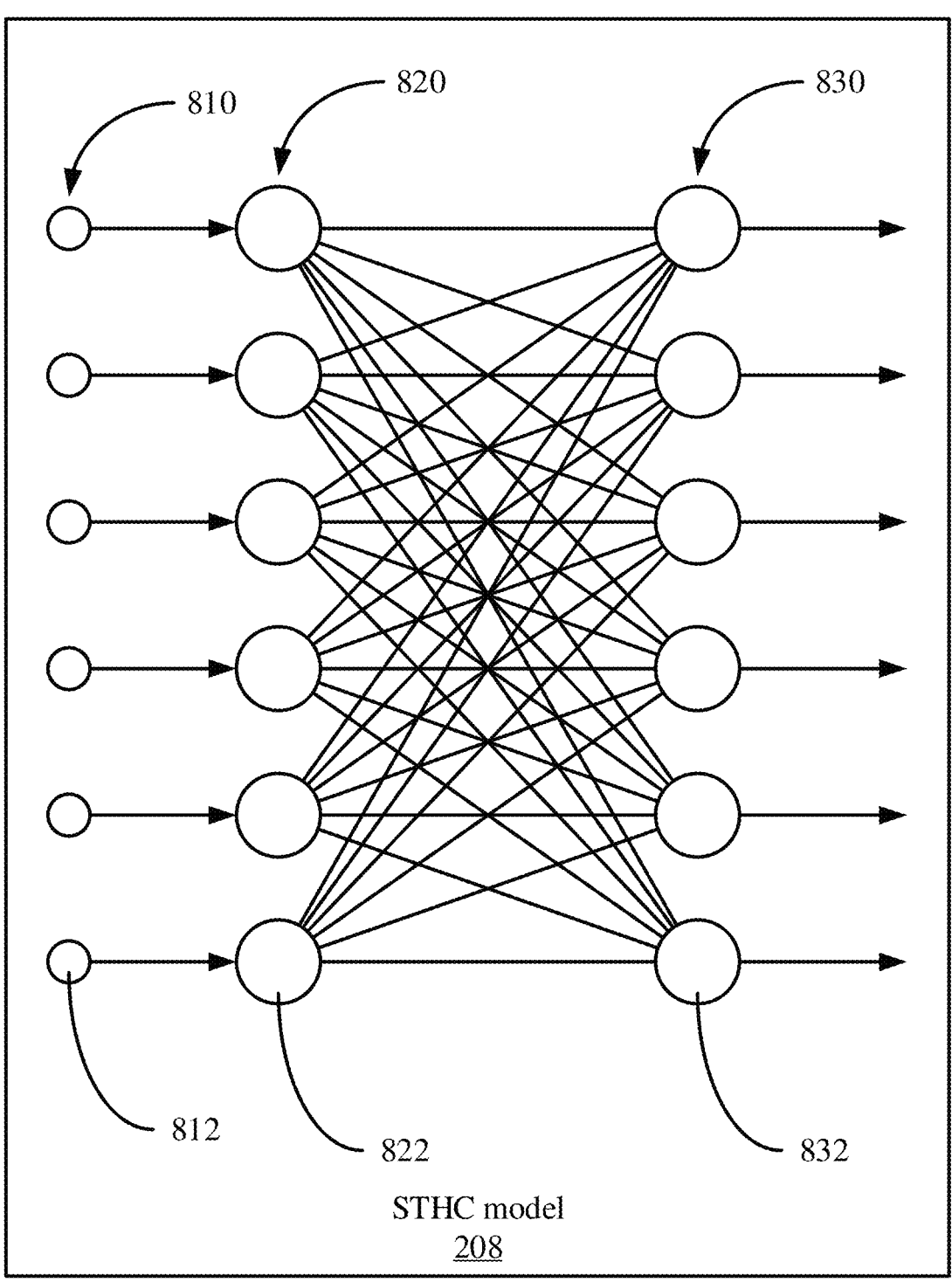
FIG. 8 is a diagram of a neural network architecture that can be used to implement part of the action recognition model, in accordance with an embodiment of the present invention.
Figure 9:
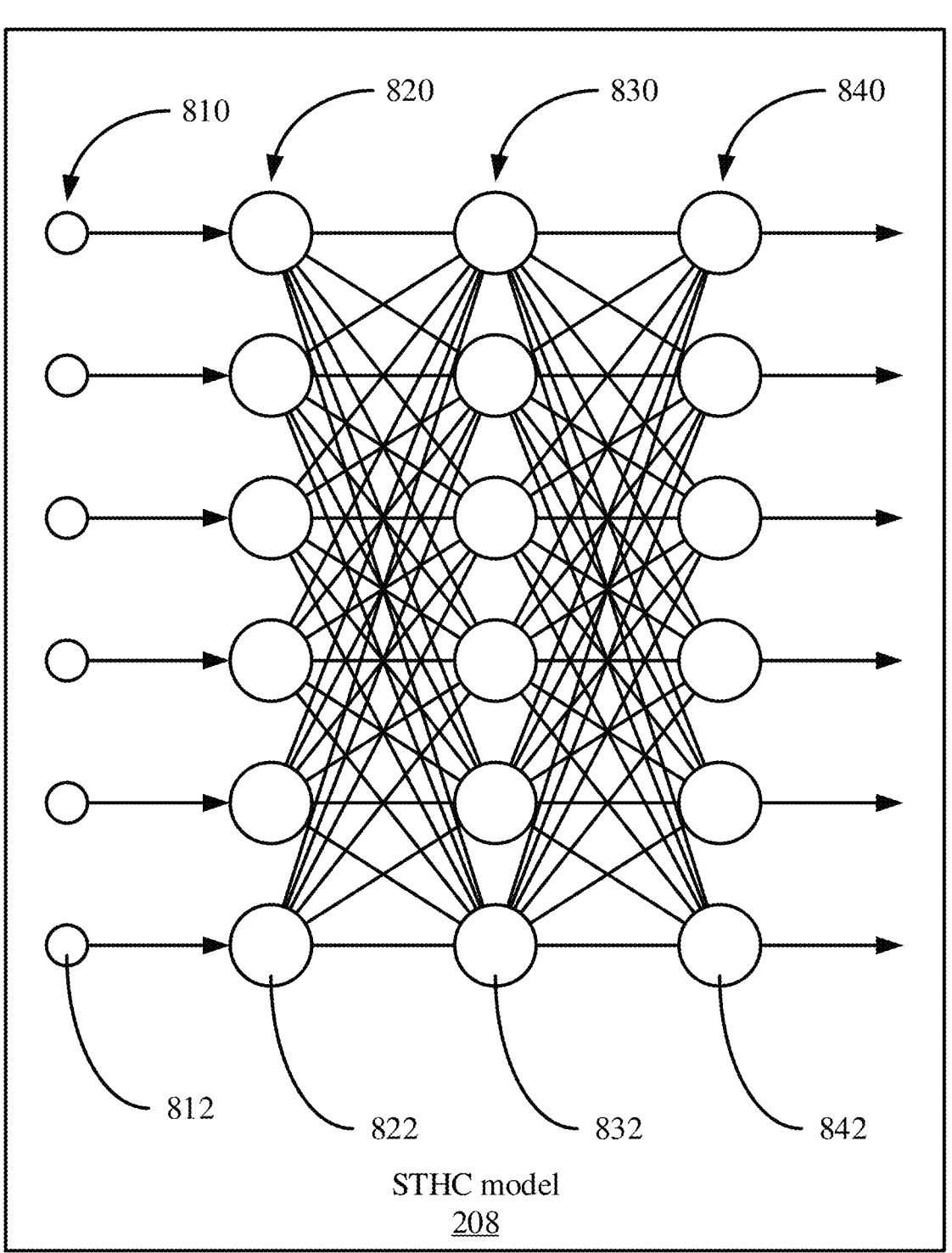
FIG. 9 is a diagram of a deep neural network architecture that can be used to implement part of the action recognition model, in accordance with an embodiment of the present invention.

Referring now to FIGS. 8 and 9, exemplary neural network architectures are shown, which may be used to implement parts of the present models, such as the STHC model 208. A neural network is a generalized system that improves its functioning and accuracy through exposure to additional empirical data. The neural network becomes trained by exposure to the empirical data. During training, the neural network stores and adjusts a plurality of weights that are applied to the incoming empirical data. By applying the adjusted weights to the data, the data can be identified as belonging to a particular predefined class from a set of classes or a probability that the input data belongs to each of the classes can be output.

The empirical data, also known as training data, from a set of examples can be formatted as a string of values and fed into the input of the neural network. Each example may be associated with a known result or output. Each example can be represented as a pair, (x, y), where x represents the input data and y represents the known output. The input data may include a variety of different data types, and may include multiple distinct values. The network can have one input node for each value making up the example's input data, and a separate weight can be applied to each input value. The input data can, for example, be formatted as a vector, an array, or a string depending on the architecture of the neural network being constructed and trained.

The neural network "learns" by comparing the neural network output generated from the input data to the known values of the examples, and adjusting the stored weights to minimize the differences between the output values and the known values. The adjustments may be made to the stored weights through back propagation, where the effect of the weights on the output values may be determined by calculating the mathematical gradient and adjusting the weights in a manner that shifts the output towards a minimum difference. This optimization, referred to as a gradient descent approach, is a non-limiting example of how training may be performed. A subset of examples with known values that were not used for training can be used to test and validate the accuracy of the neural network.

During operation, the trained neural network can be used on new data that was not previously used in training or validation through generalization. The adjusted weights of the neural network can be applied to the new data, where the weights estimate a function developed from the training examples. The parameters of the estimated function which are captured by the weights are based on statistical inference.

In layered neural networks, nodes are arranged in the form of layers. An exemplary simple neural network has an input layer 820 of source nodes 822, and a single computation layer 830 having one or more computation nodes 832 that also act as output nodes, where there is a single computation node 832 for each possible category into which the input example could be classified. An input layer 820 can have a number of source nodes 822 equal to the number of data values 812 in the input data 810. The data values 812 in the input data 810 can be represented as a column vector. Each computation node 832 in the computation layer 830 generates a linear combination of weighted values from the input data 810 fed into input nodes 820, and applies a non-linear activation function that is differentiable to the sum. The exemplary simple neural network can perform classification on linearly separable examples (e.g., patterns).

A deep neural network, such as a multilayer perceptron, can have an input layer 820 of source nodes 822, one or more computation layer(s) 830 having one or more computation nodes 832, and an output layer 840, where there is a single output node 842 for each possible category into which the input example could be classified. An input layer 820 can have a number of source nodes 822 equal to the number of data values 812 in the input data 810. The computation nodes 832 in the computation layer(s) 830 can also be referred to as hidden layers, because they are between the source nodes 822 and output node(s) 842 and are not directly observed. Each node 832, 842 in a computation layer generates a linear combination of weighted values from the values output from the nodes in a previous layer, and applies a non-linear activation function that is differentiable over the range of the linear combination. The weights applied to the value from each previous node can be denoted, for example, by $w_1, w_2, \ldots w_{n-1}, w_n$. The output layer provides the overall response of the network to the input data. A deep neural network can be fully connected, where each node in a computational layer is connected to all other nodes in the previous layer, or may have other configurations of connections between layers. If links between nodes are missing, the network is referred to as partially connected.

Training a deep neural network can involve two phases, a forward phase where the weights of each node are fixed and the input propagates through the network, and a backwards phase where an error value is propagated backwards through the network and weight values are updated.

The computation nodes 832 in the one or more computation (hidden) layer(s) 830 perform a nonlinear transformation on the input data 812 that generates a feature space. The classes or categories may be more easily separated in the feature space than in the original data space.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A method for training a model, comprising:

performing spatial augmentation on an unlabeled input video to generate spatially augmented video;

performing temporal augmentation on the input video to generate temporally augmented video;

generating predictions, using a model that was pre-trained on a labeled dataset, for the unlabeled input video, the spatially augmented video, and the temporally augmented video; and adapting parameters of the model using the predictions while enforcing temporal consistency, spatial consistency, and historical consistency, including an information maximization loss that has a first term that minimizes an entropy of probability and a second term that maximizes an entropy of a mean of predictions over videos in a target domain.

2. The method of claim 1, wherein enforcing spatial consistency includes comparing the spatially augmented video to the unlabeled input video.

3. The method of claim 1, wherein enforcing temporal consistency includes comparing the temporally augmented video to the unlabeled input video.

4. The method of claim 1, wherein enforcing historical consistency includes comparing the prediction for the unlabeled input video to a prediction of a second unlabeled video used in a prior training iteration.

5. The method of claim 1, wherein generating predictions includes performing action recognition.

6. The method of claim 5, further comprising identifying an action in treatment video relating to a rehabilitation activity of a patient and generating a report for healthcare professionals to use in decision making for rehabilitative care of the patient.

7. The method of claim 1, further comprising pre-training the model using supervised learning with the labeled dataset.

8. The method of claim 7, wherein a domain of the labeled dataset is distinct from a domain of the unlabeled dataset.

9. A system for training a model, comprising:

a hardware processor; and a memory that stores a computer program which, when executed by the hardware processor, causes the hardware processor to:

perform spatial augmentation on an unlabeled input video to generate spatially augmented video;

perform temporal augmentation on the input video to generate temporally augmented video;

generate predictions, using a model that was pre-trained on a labeled dataset, for the unlabeled input video, the spatially augmented video, and the temporally augmented video; and adapt parameters of the model using the predictions while enforcing temporal consistency, spatial consistency, and historical consistency, including an information maximization loss that has a first term that minimizes an entropy of probability and a second term that maximizes an entropy of a mean of predictions over videos in a target domain.

10. The system of claim 9, wherein the computer program further causes the hardware processor to compare the spatially augmented video to the unlabeled input video.

11. The system of claim 9, wherein the computer program further causes the hardware processor to compare the temporally augmented video to the unlabeled input video.

12. The system of claim 9, wherein the computer program further causes the hardware processor to compare the prediction for the unlabeled input video to a prediction of a second unlabeled video used in a prior training iteration.

13. The system of claim 9, wherein the generated predictions include action recognition.

14. The system of claim 13, wherein the computer program further causes the hardware processor to identify an action in treatment video relating to a rehabilitation activity of a patient and to generate a report for healthcare professionals to use in decision making for rehabilitative care of the patient.

15. The system of claim 9, wherein the computer program further causes the hardware processor to pre-train the model using supervised learning with the labeled dataset.

16. The system of claim 15, wherein a domain of the labeled dataset is distinct from a domain of the unlabeled dataset.

\* \* \* \* \*